United States Patent
Sablong et al.

[11] Patent Number: 5,986,139
[45] Date of Patent: Nov. 16, 1999

[54] PROCESS FOR THE HYDROGENATION OF IMINES

[75] Inventors: Rafaël Sablong, Brighton, United Kingdom; John Anthony Osborn, Strasbourg, France; Felix Spindler, Starrkirch-Wil, Switzerland

[73] Assignee: Novartis Crop Protection, Inc., Greensboro, N.C.

[21] Appl. No.: 09/000,172

[22] PCT Filed: Jul. 17, 1996

[86] PCT No.: PCT/EP96/03147

§ 371 Date: Jan. 26, 1998

§ 102(e) Date: Jan. 26, 1998

[87] PCT Pub. No.: WO97/05094

PCT Pub. Date: Feb. 13, 1997

[30] Foreign Application Priority Data

Jul. 27, 1995 [CH]  Switzerland ............... 2209/95

[51] Int. Cl.$^6$ ................................. C07C 209/00
[52] U.S. Cl. ............... 564/415; 564/443; 564/448; 564/489; 549/468
[58] Field of Search ................... 564/423, 443, 564/415, 448, 489; 549/68

[56] References Cited

U.S. PATENT DOCUMENTS

| | | |
|---|---|---|
| 5,112,999 | 5/1992 | Osborn et al. . |
| 5,371,256 | 12/1994 | Togni et al. . |
| 5,563,308 | 10/1996 | Spindler et al. . |

FOREIGN PATENT DOCUMENTS

| | | |
|---|---|---|
| 612758 | 8/1994 | European Pat. Off. . |
| 95/21176 | 8/1995 | WIPO . |

*Primary Examiner*—Samuel Barts
*Attorney, Agent, or Firm*—William A. Teoli, Jr.

[57] ABSTRACT

A process for the preparation of primary or secondary amines by hydrogenation of imines with hydrogen at elevated pressure and in the presence of a dinuclear Ir(III) complex having ditertiary diphosphine ligands, halide bridges, halide and hydride ligands, or an Ir(III) halide complex salt containing ditertiary diphosphine ligands, as catalyst, wherein the catalyst corresponds to formula I or Ia or to mixtures of at least two compounds of formula I, at least two compounds of formulae I and Ia, or at least two compounds of formula Ia $$[(DIP)IrX_qY_r]_2 \qquad (I),$$

$$[(DIP)X_4]^{\ominus}Me^{\oplus} \qquad (Ia),$$

wherein

DIP is the ditertiary diphosphine ligand of a ferrocenyl-diphosphine the phosphine groups of which are either bonded directly or via a bridge group —$CR_vR_w$— to the ortho positions of a cyclopentadienyl ring or are each bonded to a cyclopentadienyl ring of a ferrocenyl, so that a 5-, 6- or 7-membered ring is formed together with the Ir atom;

$R_v$ and $R_w$ are each independently of the other hydrogen, $C_1$–$C_8$alkyl, $C_1$–$C_4$fluoroalkyl, phenyl or benzyl, or are phenyl or benzyl each having from 1 to 3 $C_1$–$C_4$alkyl or $C_1$–$C_4$-alkoxy substituents;

X is Cl, Br or I;

Y is H;

q is a number 2 or 3 and r is 0 or 1, the sum of q+r being equal to 3; and $Me^{\oplus}$ is an alkali metal cation or quaternary ammonium.

27 Claims, No Drawings

PROCESS FOR THE HYDROGENATION OF IMINES

This application is a 371 of PCT/EP96/03147 filed Jul. 17, 1996.

The present invention relates to a process for the preparation of amines by hydrogenation of imines in the presence of dinuclear iridium complexes having ferrocenyl(di-tertiary phosphine) ligands.

U.S. Pat. No. 5,112,999 describes dinuclear Ir(III) complexes having ditertiary diphosphine ligands and halide bridges, halide and hydride ligands and Ir(III) halide complex salts containing a ditertiary diphosphine ligand that are suitable as catalysts for a hydrogenation of imines that may be an enantioselective hydrogenation. Ditertiary ferrocenyl-diphosphine ligands are not mentioned. U.S. Pat. No. 5,371,256 and EP-A-0 612 758 describe iridium complexes having chiral ferrocenyldiphosphine ligands for the homogeneous enantioselective hydrogenation of imines. Those homogeneous catalysis processes have proved valuable, but the activity and selectivity of the catalysts, while already high per se, are still not entirely satisfactory. It has also been suggested that soluble halides be added to the reaction mixture in order to improve the enantioselectivity and the activity and stability of the catalysts.

It has now been found that dinuclear Ir(III) complexes having ditertiary diphosphine ligands and halide bridges, halide and hydride ligands and Ir(III) halide complex salts containing a ditertiary diphosphine ligand exhibit an unexpectedly high catalyst activity and stability in the hydrogenation of imines, on their own, without further additives. Furthermore, when chiral diphosphine ligands and prochiral imines are used, extraordinarily high enantioselectivities are achieved, which may amount to an enantiomeric excess of 80% and more. The reaction times for a one hundred percent conversion may even be considerably less than an hour and, even at low catalyst concentrations, very high yields can still be achieved in relatively short reaction times.

The present invention relates to a process for the preparation of primary or secondary amines by hydrogenation of imines with hydrogen at elevated pressure and in the presence of a dinuclear Ir(III) complex having ditertiary diphosphine ligands, halide bridges, halide and hydride ligands, or an Ir(III) halide complex salt containing ditertiary diphosphine ligands, as catalyst, wherein the catalyst corresponds to formula I or Ia or to mixtures of at least two compounds of formula I, at least two compounds of formulae I and Ia, or at least two compounds of formula Ia

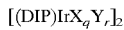  (I),

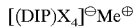  (Ia), wherein

DIP is the ditertiary diphosphine ligand of a ferrocenyl-diphosphine the phosphine groups of which are either bonded directly or via a bridge group —$CR_vR_w$— to the ortho positions of a cyclopentadienyl ring or are each bonded to a cyclopentadienyl ring of a ferrocenyl, so that a 5-, 6- or 7-membered ring is formed together with the Ir atom;

$R_v$ and $R_w$ are each independently of the other hydrogen, $C_1$–$C_8$alkyl, $C_1$–$C_4$fluoroalkyl, phenyl or benzyl, or are phenyl or benzyl each having from 1 to 3 $C_1$–$C_4$alkyl or $C_1$–$C_4$-alkoxy substituents;

X is Cl, Br or I;

Y is H;

q is the number 2 or 3 and r is 0 or 1, the sum of q+r being equal to 3; and $Me^\oplus$ is an alkali metal cation or quaternary ammonium.

The iridium compounds are preferably homogeneous catalysts that are to a large extent soluble in the reaction medium. The term "catalyst" also includes catalyst precursors which are converted into an active catalyst species at the beginning of a hydrogenation reaction.

$R_w$ is preferably hydrogen. $R_v$ is preferably $C_1$–$C_4$alkyl, for example methyl, ethyl, n-propyl or n-butyl, and especially methyl.

The ditertiary ferrocenyldiphosphine preferably contains at least one chiral group, and the diphosphine is especially an optically pure stereoisomer or a pair of diastereoisomers since, with catalysts that contain chiral ligands, optical inductions are obtained in asymmetric hydrogen reactions.

The phosphine groups preferably contain two identical or different, more preferably identical, unsubstituted or substituted hydrocarbon radicals having from 1 to 20, especially from 1 to 12, carbon atoms. Preferred diphosphines are those wherein the secondary phosphine groups contain two identical or different radicals from the following group: linear or branched $C_1$–$C_{12}$alkyl; unsubstituted or $C_1$–$C_6$alkyl- or $C_1$–$C_6$alkoxy-substituted $C_5$–$C_{12}$-cycloalkyl, $C_5$–$C_{12}$cycloalkyl—$CH_2$—, phenyl and benzyl; and phenyl and benzyl each substituted by halogen, (e.g. F, Cl and Br), $C_1$–$C_6$haloalkyl, $(C_1$–$C_{12}$alkyl$)_3$Si, $(C_6H_5)_3$Si, $C_1$–$C_6$haloalkoxy (e.g. trifluoromethoxy), —$NH_2$, phenyl$_2$N-, benzyl$_2$N-, morpholinyl, piperidinyl, pyrrolidinyl, $(C_1$–$C_{12}$alkyl$)_2$N—, -ammonium-$X_1^\ominus$, —$SO_3M_1$, —$CO_2M_1$, —$PO_3M_1$ or by —COO—$C_1$–$C_6$alkyl (e.g. —$COOCH_3$); wherein $M_1$ is an alkali metal or hydrogen and $X_1^\ominus$ is the anion of a monobasic acid. $M_1$ is preferably H, Li, Na or K. $A_1^\ominus$, as the anion of a monobasic acid, is preferably $Cl^\ominus$, $Br^\ominus$ or the anion of a carboxylic acid, for example formate, acetate, trichloroacetate or trifluoroacetate.

Examples of alkyl that preferably contains from 1 to 6 carbon atoms are methyl, ethyl, n-propyl, isopropyl, n-, iso- and tert-butyl and the isomers of pentyl and hexyl. Examples of unsubstituted or alkyl-substituted cycloalkyl are cyclopentyl, cyclohexyl, methyl- or ethyl-cyclohexyl and dimethylcyclohexyl. Examples of phenyl and benzyl each substituted by alkyl, alkoxy or by haloalkoxy are methylphenyl, dimethylphenyl, trimethylphenyl, ethylphenyl, methylbenzyl, methoxyphenyl, dimethoxyphenyl, trifluoromethylphenyl, bistrifluoromethylphenyl, tristrifluoromethylphenyl, trifluoromethoxyphenyl and bistrifluoromethoxyphenyl. Preferred phosphine groups are those which contain identical or different, preferably identical, radicals from the following group: $C_1$–$C_6$alkyl; cyclopentyl and cyclohexyl that are unsubstituted or have from one to three $C_1$–$C_4$alkyl or $C_1$–$C_4$alkoxy substituents; and benzyl and especially phenyl that are unsubstituted or have from one to three $C_1$–$C_4$alkyl, $C_1$–$C_4$alkoxy, F, Cl, $C_1$–$C_4$fluoroalkyl or $C_1$–$C_4$fluoroalkoxy substituents.

The secondary phosphine groups bonded to the cyclopentadienyl may be radicals of the formula

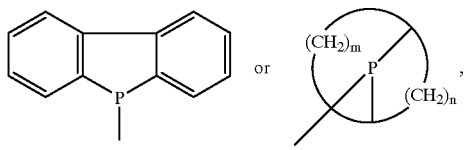

wherein m and n are each independently of the other an integer from 2 to 10 and the sum of m+n is equal to from 4 to 12, especially from 5 to 8. Examples thereof are [3.3.1]- and [4.2.1]-phobyl of the formulae

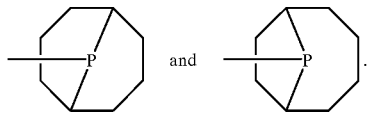

The secondary phosphine groups may also be radicals of the formula

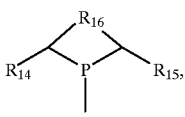

wherein $R_{16}$ is $C_1$–$C_4$alkylene, preferably $C_2$- or $C_3$-alkylene, and $R_{14}$ and $R_{15}$ are each independently of the other hydrogen, $C_1$–$C_6$alkyl, $C_1$–$C_6$alkoxy, $C_1$–$C_6$haloalkyl, $C_5$- or $C_6$-cycloalkyl, or phenyl that is unsubstituted or substituted by $C_1$–$C_4$alkyl, $C_1$–$C_4$alkoxy, $C_1$–$C_4$haloalkyl or by halogen, or benzyl that is unsubstituted or substituted by $C_1$–$C_4$alkyl, $C_1$–$C_4$alkoxy, $C_1$–$C_4$haloalkyl or by halogen. $R_{14}$ and $R_{15}$ may be, for example, methyl, ethyl, n- or iso-propyl, n-, iso- or tert-butyl, cyclohexyl, phenyl or benzyl. Halogen is preferably F or Cl. Those phosphine groups possess further chiral carbon atoms and can be used in the form of racemates or diastereoisomers. Among those phosphine ligands, those of the formula

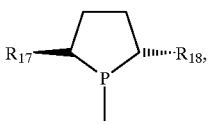

wherein $R_{17}$ and $R_{18}$ are $C_1$–$C_4$alkyl or phenyl, are especially preferred.

The ferrocenyldiphosphine preferably corresponds to formula II $$R_1R_2P\text{—}R_5\text{—}PR_3R_4 \quad (II),$$

wherein $R_1$, $R_2$, $R_3$ and $R_4$ are each independently of the others a hydrocarbon radical having from 1 to 20 carbon atoms that is unsubstituted or substituted by $C_1$–$C_6$alkyl, $C_1$–$C_6$alkoxy, halogen, $C_1$–$C_6$haloalkyl, $(C_1$–$C_{12}$alkyl$)_3$Si, $(C_6H_5)_3$Si, $C_1$–$C_6$haloalkoxy, —NH$_2$, phenyl$_2$N-, benzyl$_2$N-, morpholinyl, piperidinyl, pyrrolidinyl, $(C_1$–$C_{12}$alkyl$)_2$N-, -ammonium-$X_1^{\ominus}$, —SO$_3$M$_1$, —CO$_2$M$_1$, —PO$_3$M$_1$ or by —COO—$C_1$–$C_6$alkyl, wherein M$_1$ is an alkali metal or hydrogen and $X_1^{\ominus}$ is the anion of a monobasic acid;

$R_1$ and $R_2$ together and $R_3$ and $R_4$ together form a $C_1$–$C_4$alkylene radical that is unsubstituted or substituted by $C_1$–$C_6$alkyl, $C_1$–$C_6$alkoxy, $C_1$–$C_6$haloalkyl, $C_5$- or $C_6$-cycloalkyl, by phenyl that is unsubstituted or substituted by $C_1$–$C_4$alkyl, $C_1$–$C_4$alkoxy, $C_1$–$C_4$haloalkyl or by halogen, or by benzyl that is unsubstituted or substituted by $C_1$–$C_4$alkyl, $C_1$–$C_4$alkoxy, $C_1$–$C_4$haloalkyl or by halogen; and $R_5$ is a radical of the formula

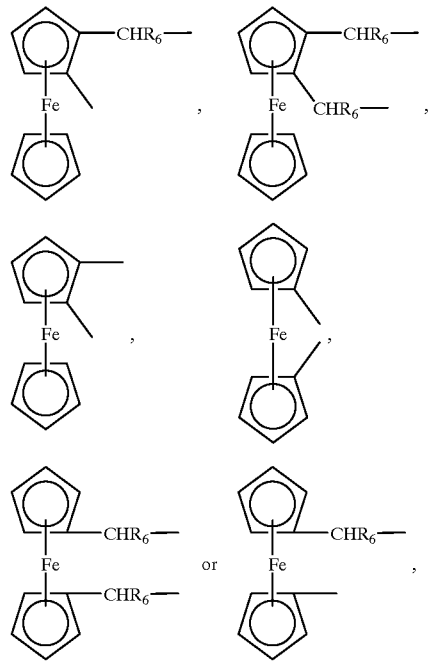

wherein $R_6$ is hydrogen, $C_1$–$C_8$alkyl, $C_1$–$C_4$fluoroalkyl, phenyl or phenyl having from 1 to 3 $C_1$–$C_4$-alkyl or $C_1$–$C_4$alkoxy substituents.

$R_1$, $R_2$, $R_3$ and $R_4$ are preferably identical or different, preferably identical, radicals from the following group: $C_1$–$C_6$alkyl; cyclopentyl and cyclohexyl that are unsubstituted or have from one to three $C_1$–$C_4$alkyl or $C_1$–$C_4$alkoxy substituents; and benzyl and especially phenyl that are unsubstituted or have from one to three $C_1$–$C_4$alkyl, $C_1$–$C_4$alkoxy, F, Cl, $C_1$–$C_4$fluoroalkyl or $C_1$–$C_4$fluoroalkoxy substituents.

Especially suitable disphosphine ligands DIP are those of formula III

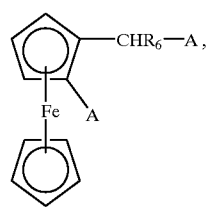

(III)

wherein $R_6$ is hydrogen and especially methyl; and

A represents identical or different groups —P(R)$_2$ wherein R is $C_1$–$C_6$alkyl, cyclohexyl, phenyl, benzyl, or phenyl or benzyl each having from one to three $C_1$–$C_4$alkyl, disubstituted amino, $C_1$–$C_4$alkoxy, —CF$_3$ or partially or completely fluorinated $C_1$–$C_4$alkoxy substituents.

R, when alkyl, is preferably branched $C_3$–$C_6$alkyl. Disubstituted amino is preferably secondary amino having from 2 to 20, and preferably from 2 to 12, carbon atoms. It may have the formula —$NR_7R_{07}$ wherein $R_7$ and $R_{07}$ are each independently of the other $C_1$–$C_6$-alkyl, unsubstituted or $C_1$–$C_4$alkyl- or $C_1$–$C_4$alkoxy-substituted $C_5$- or $C_6$-cycloalkyl, or unsubstituted or $C_1$–$C_4$alkyl- or $C_1$–$C_4$alkoxy-substituted phenyl or benzyl, or $R_7$ and $R_8$ together are tetramethylene, pentamethylene or —$(CH_2)_2$—O—$(CH_2)_2$—.

A preferred sub-group is one in which the diphosphine of formula III is chiral and $R_6$ is $C_1$–$C_4$alkyl, or phenyl or benzyl each having from one to three $C_1$–$C_4$alkyl or $C_1$–$C_4$alkoxy substituents, A represents identical or different groups —$P(R)_2$ wherein R is branched $C_3$–$C_6$alkyl, cyclohexyl, phenyl, benzyl, or phenyl or benzyl each having from one to three $C_1$–$C_4$alkyl, $C_1$–$C_4$dialkylamino, $C_1$–$C_4$alkoxy, —$CF_3$ or partially or completely fluorinated $C_1$–$C_4$alkoxy substituents. In the case of those phosphines, chirally substituted compounds wherein $R_6$ is methyl are especially preferred.

R in the group —$P(R)_2$ is, within the scope of the preferences mentioned above, especially phenyl or substituted phenyl.

Most especially preferred among those diphosphine ligands are the following, which may preferably be used in catalysts of formula (I):

{(R)-1-[(S)-2-(diphenylphosphino)ferrocenyl]}ethyl-di(3,5-dimethyl-phenyl)phosphine {(R)-1-[(S)-2-(diphenylphosphino)ferrocenyl]}ethyl-di(3,5-dimethyl-4-N,N-dipropylaminophenyl)phosphine {(R)-1-[(S)-2-(diphenylphosphino)ferrocenyl]}ethyl-di(3,5-di-iso-propyl-4-N,N-dimethylaminophenyl)phosphine {(R)-1-[(S)-2-(diphenylphosphino)ferrocenyl]}ethyl-di(3,5-di-iso-propyl-4-N,N-dibenzylylaminophenyl)phosphine {(R)-1-[(S)-2-(diphenylphosphino)ferrocenyl]}ethyl-di(3,5-dimethyl-4-N,N-dibenzylylaminophenyl)phosphine {(R)-1-[(S)-2-(diphenylphosphino)ferrocenyl]}ethyl-di(3,5-dimethyl-4-(1'-pyrrolo)phenyl)phosphine {(R)-1-[(S)-2-(diphenylphosphino)ferrocenyl]}ethyl-di(3,5-dimethyl-4-N,N-dipentylaminophenyl)phosphine {(R)-1-[(S)-2-(diphenylphosphino)ferrocenyl]}ethyl-di(3,5-dimethyl-4-N,N-dimethylaminophenyl)phosphine {(R)-1-[(S)-2-di(4-methoxyphenyl)phosphino)ferrocenyl]}ethyl-di(3,5-dimethyl-4N,N-dimethylaminophenyl) phosphine and especially {(R)-1-[(S)-2-(diphenylphosphino)ferrocenyl]}ethyl-di(3,5-dimethyl-phenyl)phosphine.

The preparation of ferrocenyldiphosphine ligands is described, for example, in EP-A-0 564 406 and by T. Hayashi et al. in Bull. Chem. Soc. Jpn., 53, pages 1136–1151, and by A. Togni et al. in J. Am. Chem. Soc., 116, pages 4062 to 4066 (1994) and in Inorg. Chim. Acta, 222, pages 213 to 224.

In formulae I and Ia, X is preferably Br and especially I. Also in formulae I and Ia, q is 2 or 3and r is 1.

$M^{\oplus}$ in formula Ia may be $(C_1$–$C_6alkyl)_4N^{\oplus}$, $Li^{\oplus}$, $Na^{\oplus}$ or $K^{\oplus}$.

In an especially preferred form of the process of the invention, the catalysts are those of formula Ib $$[(DIP)IrI_2H]_2 \quad (Ib),$$

wherein DIP is as defined hereinbefore, including the preferred definitions.

The iridium catalysts to be used according to the invention may be prepared according to the processes described in U.S. Pat. No. 5,112,999.

Suitable imines are especially those which contain at least one

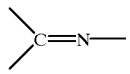

group. If the groups are substituted asymmetrically and are thus compounds having a prochiral ketimine group, it is possible in the process of the invention for mixtures of optical isomers or pure optical isomers to be formed if enantioselective or diastereoselective iridium catalysts are used. The imines may contain further chiral carbon atoms. The free bonds in the above formulae may be saturated with hydrogen or organic radicals having from 1 to 22 carbon atoms or organic hetero radicals having from 1 to 20 carbon atoms and at least one hetero atom from the group O, S, N and P. The nitrogen atom of the group

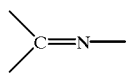

may also be saturated with $NH_2$ or a primary amino group having from 1 to 22 carbon atoms or a secondary amino group having from 2 to 40 carbon atoms. The organic radicals may be substituted, for example, by F, Cl, Br, $C_1$–$C_4$haloalkyl, wherein halogen is preferably F or Cl, —CN, —$NO_2$, —$CO_2H$, —$CONH_2$, —$SO_3H$, —$PO_3H_2$, or by $C_1$–$C_{12}$alkyl esters, $C_1$–$C_{12}$alkyl amides, phenyl esters or benzyl esters of the groups —$CO_2H$, —$SO_3H$ and —$PO_3H_2$. Aldimine and ketimine groups are especially reactive and therefore a selective hydrogenation of

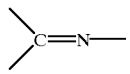

groups in addition to the groups

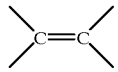

and/or

is possible with the process of the invention. Aldimine and ketimine groups are also be understood as including hydrazone groups

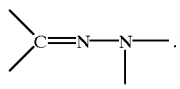

The process of the invention is suitable especially for the hydrogenation of aldimines, ketimines and hydrazones with the formation of corresponding amines and hydrazines. The ketimines are preferably N-substituted. It is preferable to use chiral iridium catalysts and to hydrogenate enantiomerically pure, chiral or prochiral ketimines to prepare optical isomers, the optical yields (enantiomeric excess, ee) being, for example, higher than 30%, preferably higher than 50%, and it being possible to obtain yields of more than 90%. The optical yield indicates the ratio of the two stereoisomers formed, which ratio may be, for example, greater than 2:1 and preferably greater than 4:1.

The imines are preferably imines of formula IV

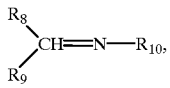

(IV)

which are hydrogenated to form amines of formula V

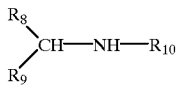

(V)

wherein $R_{10}$ is preferably a substituent;
and wherein $R_{10}$ is preferably linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and $NR_{11}$; a $C_7$–$C_{16}$aralkyl bonded via an alkyl carbon atom, or $C_1$–$C_{12}$alkyl substituted by said cycloalkyl or heterocycloalkyl or heteroaryl;
or wherein $R_{10}$ is $C_6$–$C_{12}$aryl, or $C_4$–$C_{11}$heteroaryl bonded via a ring carbon atom and having 1 or 2 hetero atoms in the ring; $R_{10}$ being unsubstituted or substituted by —CN, —NO$_2$, F, Cl, $C_1$–$C_{12}$alkyl, $C_1$–$C_{12}$alkoxy, $C_1$–$C_{12}$alkylthio, $C_1$–$C_6$haloalkyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —CONR$_{12}$R$_{13}$ or by —COOR$_{12}$, and the aryl radicals and the aryl groups in aralkyl, aralkoxy and aralkylthio in turn being unsubstituted or substituted by —CN, —NO$_2$, F, Cl, $C_1$–$C_4$-alkyl, -alkoxy, -alkylthio, —OH, —CONR$_{12}$R$_{13}$ or by —COOR$_{12}$;

$R_{12}$ and $R_{13}$ are each independently of the other hydrogen, $C_1$–$C_{12}$alkyl, phenyl or benzyl, or $R_{12}$ and $R_{13}$ together are tetra- or penta-methylene or 3-oxapentylene;

$R_{11}$ has independently the same meaning as given for $R_{12}$;

$R_8$ and $R_9$ are each independently of the other a hydrogen atom, $C_1$–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —CONR$_{12}$R$_{13}$ or by —COOR$_{12}$; $C_6$–$C_{12}$aryl or $C_7$–$C_{16}$aralkyl each of which is unsubstituted or substituted as $R_{10}$, or —CONR$_{12}$R$_{13}$ or —COOR$_{12}$ wherein $R_{12}$ and $R_{13}$ are as defined hereinbefore; or $R_{10}$ is as defined hereinbefore and $R_8$ and $R_9$ together are alkylene having from 2 to 5 carbon atoms that is optionally interrupted by 1 or 2 —O—, —S— or —NR$_6$— radicals, and/or unsubstituted or substituted by =O or as indicated above for $R_8$ and $R_9$ in the meaning of alkyl, and/or condensed with benzene, pyridine, pyrimidine, furan, thiophene or pyrrole; or $R_9$ is as defined hereinbefore and $R_8$ and $R_{10}$ together are alkylene having from 2 to 5 carbon atoms that is optionally interrupted by 1 or 2 —O—, —S— or —NR$_{11}$— radicals, and/or unsubstituted or substituted by =O or as indicated above for $R_8$ and $R_9$ in the meaning of alkyl, and/or condensed with benzene, pyridine, pyrimidine, furan, thiophene or pyrrole.

The radicals $R_8$, $R_9$ and $R_{10}$ may contain one or more centres of chirality.

$R_8$, $R_9$ and $R_{10}$ may be substituted in any desired positions by identical or different radicals, for example by from 1 to 5, preferably from 1 to 3, substituents.

Suitable substituents for $R_8$ and for $R_9$ and $R_{10}$ are:

$C_1$–$C_{12}$-, preferably $C_1$–$C_6$- and especially $C_1$–$C_4$-alkyl, -alkoxy or -alkylthio, e.g. methyl, ethyl, propyl, n-, iso- and tert-butyl, the isomers of pentyl, hexyl, octyl, nonyl, decyl, undecyl and dodecyl, and corresponding alkoxy and alkylthio radicals;

$C_1$–$C_6$-, preferably $C_1$–$C_4$-haloalkyl having preferably F and Cl as halogen, e.g. trifluoro- or trichloro-methyl, difluorochloromethyl, fluorodichloromethyl, 1,1-difluoroeth-1-yl, 1,1-dichloroeth-1-yl, 1,1,1-trichloro- or 1,1,1-trifluoroeth-2-yl, pentachloroethyl, pentafluoroethyl, 1,1,1-trifluoro-2,2-dichloroethyl, n-perfluoropropyl, iso-perfluoropropyl, n-perfluorobutyl, fluoro- or chloro-methyl, difluoro- or dichloro-methyl, 1-fluoro- or 1-chloro-eth-2-yl or -eth-1-yl, 1-, 2- or 3-fluoro- or 1-, 2- or 3-chloro-prop-1-yl or -prop-2-yl or -prop-3-yl, 1-fluoro- or 1-chloro-but-1-yl, -but-2-yl, -but-3-yl or -but-4-yl, 2,3-dichloroprop-1-yl, 1-chloro-2-fluoro-prop-3-yl, 2,3-dichlorobut-1-yl;

$C_6$–$C_{12}$-aryl, -aryloxy or -arylthio, in which aryl is preferably naphthyl and especially phenyl, $C_7$–$C_{16}$-aralkyl, -aralkoxy and -aralkylthio, in which the aryl radical is preferably naphthyl and especially phenyl and the alkylene radical is linear or branched and contains from 1 to 10, preferably from 1 to 6 and especially from 1 to 3, carbon atoms, for example benzyl, naphthylmethyl, 1- or 2-phenyl-eth-1-yl or -eth-2-yl, 1-, 2- or 3-phenyl-prop-1-yl, -prop-2-yl or -prop-3-yl, with benzyl being especially preferred;

the radicals containing the aryl groups mentioned above may in turn be mono- or poly-substituted, for example by $C_1$–$C_4$-alkyl, -alkoxy or -alkylthio, halogen, —OH, —CONR$_{12}$R$_{13}$ or by —COOR$_{12}$, wherein $R_{12}$ and $R_{13}$ are as defined; examples are methyl, ethyl, n- and iso-propyl, butyl, corresponding alkoxy and alkylthio radicals, F, Cl, Br, dimethyl-, methylethyl- and diethyl-carbamoyl and methoxy-, ethoxy-, phenoxy- and benzyloxy-carbonyl;

halogen, preferably F and Cl;

secondary amino having from 2 to 24, preferably from 2 to 12 and especially from 2 to 6, carbon atoms, the secondary amlino preferably containing 2 alkyl groups, for example dimethyl-, methylethyl-, diethyl-, methylpropyl-, methyl-n-butyl-, di-n-propyl-, di-n-butyl-, di-n-hexyl-amino;

—CONR$_{12}$R$_{13}$, wherein $R_{12}$ and $R_{13}$ are each independently of the other $C_1$–$C_{12}$-, preferably $C_1$–$C_6$-, and especially $C_1$–$C_4$-alkyl, or $R_{12}$ and $R_{13}$ together are tetra- or penta-methylene or 3-oxapentylene, the alkyl being linear or branched, e.g. dimethyl-, methylethyl-, diethyl-, methyl-n-propyl-, ethyl-n-propyl-, di-n-propyl-, methyl-n-butyl-, ethyl-n-butyl-, n-propyl-n-butyl- and di-n-butyl-carbamoyl;

—COOR$_{12}$, wherein $R_{12}$ is $C_1$–$C_{12}$-, preferably $C_1$–$C_6$-alkyl, which may be linear or branched, e.g. methyl, ethyl, n- and iso-propyl, n-, iso- and tert-butyl, and the isomers of pentyl, hexyl, heptyl, octyl, nonyl, decyl, undecyl and dodecyl.

$R_8$, $R_9$ and $R_{10}$ may contain especially functional groups, such as keto groups, —CN, —NO$_2$, carbon double bonds, N—O—, aromatic halogen groups and amide groups.

$R_8$ and $R_9$ as heteroaryl are preferably a 5- or 6-membered ring having 1 or 2 identical or different hetero atoms, especially O, S or N, which contains preferably 4 or 5 carbon atoms and can be condensed with benzene. Examples of heteroaromatics from which $R_8$ and $R_9$ can be derived are furan, pyrrole, thiophene, pyridine, pyrimidine, indole and quinoline.

$R_8$ and $R_9$ as heteroaryl-substituted alkyl are derived preferably from a 5- or 6-membered ring having 1 or 2 identical or different hetero atoms, especially O, S or N, that contains preferably 4 or 5 carbon atoms and can be condensed with benzene. Examples of heteroaromatics are furan, pyrrole, thiophene, pyridine, pyrimidine, indole and quinoline.

$R_8$ and $R_9$ as heterocycloalkyl or as heterocycloalkyl-substituted alkyl contain preferably from 4 to 6 ring atoms and 1 or 2 identical or different hetero atoms from the group O, S and $NR_{11}$. It can be condensed with benzene. It may be derived, for example, from pyrrolidine, tetrahydrofuran, tetrahydrothiophene, indane, pyrazolidine, oxazolidine, piperidine, piperazine or morpholine.

$R_8$, $R_9$ and $R_{10}$ as alkyl are preferably unsubstituted or substituted $C_1$–$C_6$-, especially $C_1$–$C_4$-alkyl, which may be linear or branched. Examples are methyl, ethyl, iso- and n-propyl, iso-, n- and tert-butyl, the isomers of pentyl, hexyl, heptyl, octyl, nonyl, decyl, undecyl and dodecyl.

$R_8$, $R_9$ and $R_{10}$ as unsubstituted or substituted cycloalkyl contain preferably from 3 to 6, especially 5 or 6, ring carbon atoms. Examples are cyclopropyl, cyclobutyl, cyclopentyl, cyclohexyl, cycloheptyl and cyclooctyl.

$R_8$, $R_9$ and $R_{10}$ as aryl are preferably unsubstituted or substituted naphthyl and especially phenyl. $R_8$, $R_9$ and $R_{10}$ as aralkyl are preferably unsubstituted or substituted phenylalkyl having from 1 to 10, preferably from 1 to 6 and especially from 1 to 4, carbon atoms in the alkylene, the alkylene being linear or branched. Examples are especially benzyl, and 1-phenyleth-1-yl, 2-phenyleth-1-yl, 1-phenylprop-1-yl, 1-phenylprop-2-yl, 1-phenylprop-3-yl, 2-phenylprop-1-yl, 2-phenylprop-2-yl and 1-phenylbut-4-yl.

In $R_9$ and $R_{10}$ as —$CONR_{12}R_{13}$ and —$COOR_{12}$, $R_{12}$ and $R_{13}$ are preferably $C_1$–$C_6$-, especially $C_1$–$C_4$-alkyl, or $R_{12}$ and $R_{13}$ together are tetramethylene, pentamethylene or 3-oxapentylene. Examples of alkyl are mentioned hereinbefore.

$R_8$ and $R_9$ together or $R_8$ and $R_{10}$ together as alkylene are preferably interrupted by 1 —O—, —S— or —$NR_{11}$—, preferably —O—. $R_8$ and $R_9$ together or $R_8$ and $R_{10}$ together form, with the carbon atom or with the —N═C group to which they are respectively bonded preferably a 5- or 6-membered ring. For the substituents the preferences mentioned hereinbefore apply. As condensed alkylene, $R_8$ and $R_9$ together or $R_8$ and $R_{10}$ together are preferably alkylene condensed with benzene or pyridine. Examples of alkylene are: ethylene, 1,2- or 1,3-propylene, 1,2-, 1,3- or 1,4-butylene, 1,5-pentylene and 1,6-hexylene. Examples of interrupted or ═O-substituted alkylene are 2-oxa-1,3-propylene, 2-oxa-1,4-butylene, 2-oxa- or 3-oxa- 1,5-pentylene, 3-thia-1,5-pentylene, 2-thia-1,4-butylene, 2-thia-1,3-propylene, 2-methylimino-1,3-propylene, 2-ethylimino-1,4-butylene, 2- or 3-methylimino-1,5-pentylene, 1-oxo-2-oxa-1,3-propylene, 1-oxo-2-oxa-1,4-butylene, 2-oxo-3-oxa-1,4-butylene and 1-oxa-2-oxo-1,5-pentylene. Examples of condensed alkylene are:

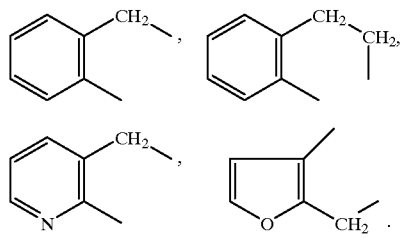

Examples of condensed and interrupted and unsubstituted or ═O-substituted alkylene are:

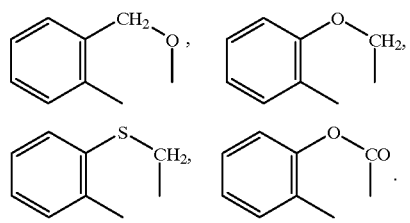

$R_{12}$ and $R_{13}$ are preferably each independently of the other hydrogen, $C_1$–$C_4$alkyl, phenyl or benzyl. $R_{11}$ is preferably hydrogen or $C_1$–$C_4$alkyl.

A further preferred group is formed by prochiral imines in which in formula IV $R_8$ and $R_9$ are different from each other.

In an especially preferred group, in formula IV $R_{10}$ is 2,6-di-$C_1$–$C_4$alkylphen-1-yl and especially 2,6-dimethylphen-1-yl or 2-methyl-6-ethylphen-1-yl, $R_8$ is $C_1$–$C_4$alkyl and especially ethyl or methyl, and $R_9$ is $C_1$–$C_4$alkyl, $C_1$–$C_4$alkoxymethyl or $C_1$–$C_4$alkoxyethyl, and especially methoxymethyl.

Of those compounds, imines of formulae

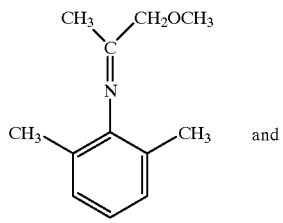
(VIa)

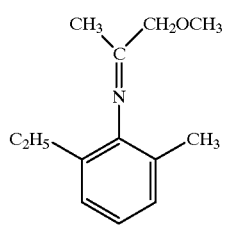
(VIb)

and are especially important, as is the imine of formula

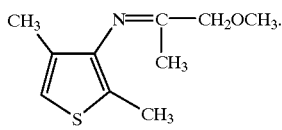
(VIc)

Imines of formula IV are known or they can be prepared in accordance with known processes from aldehydes or ketones and primary amines.

The molar ratio of imine to iridium catalyst may be, for example, from 1 000 000 to 10, especially from 500 000 to 20, more preferably from 200 000 to 100 and most preferably from 100 000 to 100.

The process is carried out preferably at a temperature of from −20 to 100° C., especially from 0 to 80° C. and more especially from 10 to 70° C., and preferably at a hydrogen pressure of from $2 \times 10^5$ to $1.5 \times 10^7$ Pa (5 to 150 bar), especially from $10^6$ to $10^7$ Pa (10 to 100 bar).

The reaction can be carried out in the absence or in the presence of solvents. Suitable solvents, which can be used alone or as a mixture of solvents, are, for example:

aliphatic and aromatic hydrocarbons, such as pentane, hexane, cyclohexane, methylcyclohexane, benzene, toluene and xylene; ethers, such as diethyl ether, diethylene glycol dimethyl ether, tetrahydrofuran and dioxane; halogenated hydrocarbons, such as methylene chloride, chloroform, 1,1,2,2-tetrachloroethane and chlorobenzene; esters and lactones, such as ethyl acetate, butyrolactone and valerolactone; acid amides and lactams, such as dimethylformamide, dimethylacetamide and N-methylpyrrolidone, and ketones, such as acetone, dibutyl ketone, methyl isobutyl ketone and methoxyacetone.

In detail, the process according to the invention can be carried out by first dissolving the catalyst in a solvent or in a portion of the substance to be hydrogenated and then adding the imine (where appropriate as a solution). That mixture is hydrogenated in an autoclave and the reaction mixture is isolated and purified in a manner known per se, for example by precipitation, extraction or distillation. The catalyst may be formed in situ in the starting phase of the hydrogenation.

Before the hydrogenation reaction, a protective gas atmosphere is advantageously used. It is advantageous to ensure that the catalyst solution stands for only a short time, and to carry out the hydrogenation of the imines as soon as possible after the preparation of the catalyst solution.

In the case of the hydrogenation of aldimines and ketimines, the aldimines and ketimines can also be formed in situ before or during the hydrogenation. In a preferred form, an amine and an aldehyde or a ketone are mixed together and added to the catalyst solution and the aldimine or ketimine formed in situ is hydrogenated. It is also possible, however, to use an amine, a ketone or an aldehyde together with the catalyst as the initial batch and to add the ketone or the aldehyde or the amine thereto, either all at once or in metered amounts.

The hydrogenation can be carried out continuously or batchwise in various types of reactor. Preference is given to those reactors which allow comparatively good intermixing and good removal of heat, such as, for example, loop reactors. That type of reactor has proved to be especially satisfactory when small amounts of catalyst are used.

The process according to the invention yields the corresponding amines in short reaction times while having chemically a high degree of conversion, with surprisingly excellent optical yields (ee) of 70% or more being obtained even at relatively high temperatures of more than 50° C., and even with high molar ratios of imine to catalyst.

The hydrogenated organic compounds that can be prepared in accordance with the invention, for example the amines, are biologically active substances or are intermediates for the preparation of such substances, especially in the field of the preparation of pharmaceuticals and agrochemicals. For example, o,o-dialkylarylketamine derivatives, especially those having alkyl and/or alkoxyalkyl groups, are effective as fungicides, especially as herbicides. The derivatives may be amine salts, acid amides, for example of chloroacetic acid, tertiary amines and ammonium salts (see, for example, EP-A-0 077 755 and EP-A-0 115 470).

Especially important in this connection are the optically active amines of formula VII

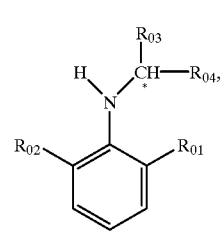
(VII)

which can be prepared using the processes according to the invention from the imines of formula (VI) in the presence of asymmetric iridium catalysts, and wherein $R_{01}$, $R_{02}$ and $R_{03}$ are each independently of the others $C_1$–$C_4$alkyl, and $R_{04}$ is $C_1$–$C_4$alkyl or $C_1$–$C_4$-alkoxymethyl or $C_1$–$C_4$alkoxyethyl, and especially the amines of the formulae

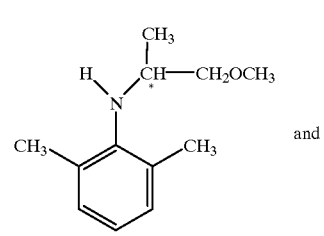
(VIIa)

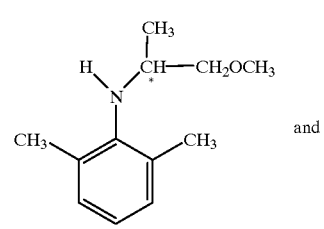
(VIIa)

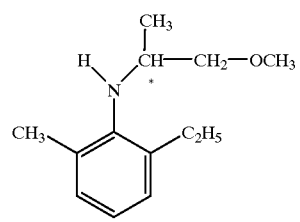
(VIIb)

which can be prepared from the imines of formulae (VIa) and (VIb) and can be converted in accordance with methods that are customary per se with chloroacetic acid into the desired herbicides of the chloroacetanilide type; of those compounds, the compounds having the S-configuration at the asymmetric C* atom are most especially preferred.

The Examples that follow illustrate the invention in more detail. The chemical conversion is determined by gas chromatography (column 2 m OV 101 / 100 to 200° C. at 10° C./min). The optical yields (enantiomeric excess, ee) are determined either by gas chromatography [Chirasil-Val column, 50 m, manufacturer: Alltech, USA, T=150° C., isothermic], by HPLC (Chiracel OD column) or by $^1$H-NMR spectroscopy (using shift reagents).

For the diphosphines, the following abbreviations are used:

{(R)-1-[(S)-2-(diphenylphosphino)ferrocenyl]}ethyl-bis[(3,5-dimethyl)phenyl]phosphine [PPF-P(xyl)$_2$]

{(R)-1-[(S)-2-(diphenylphosphino)ferrocenyl]}ethyl-bis[(3,5-dimethyl-4-dimethylamino)phenyl]phosphine [PPF-P(NMe$_2$xyl)$_2$]

{(R)-1-[(S)-2-(diphenylphosphino)ferrocenyl]}ethyl-di-(tertiary butyl)phosphine [PPF-P(t-Bu)$_2$]

A) Preparation of starting compounds and catalysts

EXAMPLE A1

Preparation of [(PPF-P(xyl)$_2$)Ir(cyclooctadiene)]BF$_4$ (A1)

320 mg (1.64 mmol) of AgBF$_4$ are added to a solution of 525 mg (0.78 mmol) of [Ir(cyclooctadiene)Cl]$_2$ in 10 ml of methylene chloride and stirred. After 15 minutes, 1 g (1.57 mmol) of PPF-P(xyl)$_2$ in 10 ml of methylene chloride is slowly added dropwise. The deep-red solution formed is stirred at room temperature for 12 h with the exclusion of light. It is then filtered over Celite and the solvent is evaporated off in vacuo to yield 1.54 g (96%) of a deep-red solid (A1).

$^{31}$P{$^1$H}-NMR (121 MHz; CDCl$_3$) 40.34 and 8.68 (AX; $^2$J$_{PP}$32 21.9 and 23.6 Hz; 92%); 6.49 and 25.11 (AX; $^2$J$_{PP}$=23.96 and 23.63 Hz; 6%); 18.87 (s; 2%).

EXAMPLE A2

Preparation of [(PPF-P(NMe$_2$xyl)$_2$)Ir(cyclooctadiene)]BF$_4$ (A2)

Preparation is effected analogously to Example A1. The isolated product contains, according to the NMR spectrum, approximately 10% by-products.

$^{31}$P{$^1$H}-NMR (121 MHz; CDCl$_3$) 39.76 and 10.24 (AX; $^2$J$_{PP}$=21.5 and 21.0 Hz)

EXAMPLE A3

Preparation of [(PPF-P(t-Bu)$_2$)Ir(cyclooctadiene)]BF$_4$ (A3)

Preparation is effected analogously to Example A1. The isolated product contains, according to the NMR spectrum, approximately 10% by-products.

$^{31}$P{$^1$H}-NMR (121 MHz; CDCl$_3$). 61.38 and 9.52 (AX; $^2$J$_{PP}$=10.5 and 17.7 Hz)

EXAMPLE A4

Preparation of [(PPF-P(xyl)$_2$)IrHI$_2$]$_2$ (Ir1)

a) 6.5 g (48.6 mmol) of LiI are added to a solution of 1.5 mmol of compound A1 in 20 ml of acetone and the mixture is then refluxed with stirring for 5 h. After cooling, the solvent is removed using a rotary evaporator. The orange-red residue is dissolved in 100 ml of methylene chloride, left to stand at room temperature for 12 h, and the white precipitate which forms is removed by filtration. The filtrate is washed twice with 100 ml of water and the solvent is then removed using a rotary evaporator. The orange-brown residue is taken up in 20 ml of methylene chloride, 50 ml of pentane are added thereto and the orange-brown precipitate is removed by filtration. The filtrate is again concentrated to dryness, taken up in 5 ml of methylene chloride, 20 ml of pentane are added thereto and the red-brown precipitate is removed by filtration. The last procedure is repeated, and the three precipitates are combined, washed with 10 ml of water, twice with 10 ml of ethanol, twice with 5 ml of diethyl ether and three times with 10 ml of pentane. 1.35 g (83%) of an orange-brown solid are obtained as a mixture of isomers.

$^1$H-NMR (300 MHz; CDCl$_3$) Hydride region: Main isomer −17.25 (dd, ΣJ=25.5 Hz, 73%) Other resonances: −16.15 (m, broad, 5%); −16.22 (dd, ΣJ=24.6 Hz, 6%); −19.16 (t, $^2$J$_P$=16.1 Hz, 6%); −19.72 (t, $^2$J$_P$=16.1 Hz, 5%); 20.86 (dd, ΣJ=28.9 Hz, 5%) ppm.

b) 450 mg (0.44 mmol) of compound A1 and 1.5 g of LiI (26 equivalents) are mixed with 10 ml of acetone, the mixture is refluxed for 2 h and then the solvent is removed to yield a deep-red solid comprising 2 position isomers as the main products, which are separated as follows:

First the residue is dried under a high vacuum for 12 h, then 20 ml of methylene chloride are added, the insoluble constituents are removed by filtration and the solvent is removed in vacuo. That procedure is repeated three times. Then 5 ml of toluene are added and the yellow-orange solution is decanted from the dark red oil which has separated. The procedure is repeated twice. The three filtrates are combined and concentrated to dryness by evaporation. 5 ml of toluene are added, the yellow solution is decanted from the red oil and the procedure is repeated. The filtrates and oil fractions are combined. 30 ml of pentane are added to the yellow toluene solution (10 ml) and the yellow solid which precipitates is removed by filtration. The filtrate is concentrated by evaporation, dissolved with 4 ml of toluene, 30 ml of pentane are added and the yellow solid which precipitates is then removed by filtration. The filtrate is concentrated by evaporation and the brown solid is washed twice with 2 ml of ethanol and twice with 2 ml of diethyl ether. After drying, 65 mg (14%) of compound Ir2 are obtained in the form of a fawn-coloured solid.

$^1$H-NMR (300 MHz; CDCl$_3$) Hydride region: Main isomer −17.22 (dd, ΣJ=25.6 Hz, 92%)

$^{31}$P{$^1$H}-NMR (121 MHz; CDCl$_3$). Main isomer. 10.4 and −22.2 (AX; $^2$J$_{PP}$=18.5 and 15.8 Hz, 92%).

The red oil is dried in vacuo and dissolved in methylene chloride, and undissolved portions are removed by filtration. The solvent is then evaporated off and the procedure is repeated twice. 270 mg (57%) of compound Ir3 are obtained in the form of a reddish brown solid.

$^1$H-NMR (300 MHz; CDCl$_3$) Hydride region: Main isomer −19.74 (t, $^2$J$_{HP}$=16.3 Hz, 84%)

$^{31}$P{$^1$H}-NMR (121 MHz; CDCl$_3$). Main isomer: 15.5 and −8.6 (AX; $^2$J$_{PP}$=12.5 and 12.8 Hz, 84%). EXAMPLE A5

Preparation of [(PPF-P(NMe$_2$xyl)$_2$)IrHI$_2$]$_2$ (Ir4)

1.4 g (39 equivalents) of LiI are added to a solution of 0.134 mmol of compound A2 in 8 ml of acetone and the mixture is refluxed with stirring for 5 h. It is then concentrated using a rotary evaporator to a volume of 4 ml and the yellow-orange solid residue is separated off by centrifuging. The solid is washed twice with 2 ml of acetone, with 2 ml of methylene chloride, with 2 ml of chloroform and twice with 5 ml of pentane. After drying in vacuo, 125 mg (40%) of a yellow-orange solid are obtained.

$^1$H-NMR (300 MHz; CD$_3$CN) Hydride region: −20.51 (t, $^2J_{HP}$=16.1 Hz, 87%); −20.28 t, $^2J_{HP}$=17.0 Hz, 13%).

$^{31}$P{$^1$H}-NMR (121 MHz; CD$_3$CN) 11.8 and −14.4 (s, 85%); 8.1 and −16.4 (m, 15%).

EXAMPLE A6

Preparation of [(PPF-P(t-Bu)$_2$)IrHI$_2$]$_2$ (Ir5)

2.6 g of LiI (19.43 mmol) are added to a solution of 0.245 mmol of compound A3 in 15 ml of acetone and the mixture is then refluxed with stirring for 8 h. The solvent is then removed using a rotary evaporator and the dark red solid residue is dried under a high vacuum. The solid is dissolved in 20 ml of methylene chloride and the insoluble constituents are removed by filtration. That procedure is repeated twice. The residue is again taken up in methylene chloride and washed twice with 10 ml of water. The methylene chloride is then removed using a rotary evaporator and the reddish brown residue is washed three times with 10 ml of ethanol and three times with 10 ml of diethyl ether. After drying in vacuo, 450 mg (93%) of a reddish brown solid are obtained.

$^1$H-NMR (300 MHz; CDCl$_3$) Hydride region: −18.88 (dd,$\Sigma^2J_{HP}$=32 Hz, 40%); −21.48 (t, $^2J_{HP}$=15.5 Hz, 60%).

$^{31}$P{$^1$H}-NMR (121 MHz; CDCl$_3$) 60.4 and 8.0 (s, broad, 40%); 54.8 and −9.9 (s, broad, 60%).

B) Hydrogenation of imines

The following abbreviations are used for the imines used:

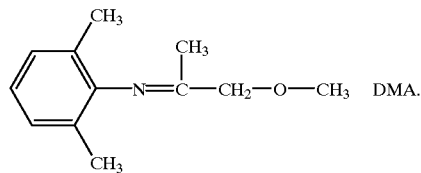
DMA.

EXAMPLES B1–B13

In a 50 ml steel autoclave, the catalyst (0.0157 mmol) is dissolved in 2.5 ml of methylene chloride and 7.5 ml of tetrahydrofuran. The imine (7.83 mmol, 500 equivalents) is added to the solution. The autoclave is degassed three times with hydrogen at 25 bar. The reaction mixture is then heated to 30° C. and hydrogen is passed in under pressure. To examine the course of the reaction, samples may be taken periodically via a built-in cannula. $t_{Con}$ is the time taken before the conversion indicated is reached and $t_{End}$ is the total reaction time. S/Ir is the molar ratio of DMA to iridium catalyst. Ir denotes the iridium catalysts Ir1 to Ir5 according to Examples A4 to A6. In Examples B3 and B10 tetrahydrofuran is used, in Example B4 methylene chloride, in Example B5 toluene, and in Example B6 methyl tert-butyl ether. The results are given in Table 1.

TABLE 1

| Ir | S/Ir | H$_2$ pressure (bar) | $t_{Con}$ (% conversion) | $t_{End}$ | Yield (%) | Optical Yield (% ee) | Example |
|---|---|---|---|---|---|---|---|
| Ir1 | 500 | 40 | 15'(82) | 25' | 98 | 82(S) | B1 |
| Ir1 | 500 | 10 | 30'(51) | 1h15 | 98 | 82(S) | B2 |
| Ir1 | 500 | 10 | 30'(61) | 1h | 98 | 81(S) | B3 |
| Ir1 | 500 | 10 | 1h (40) | 3h25 | 80 | 77(S) | B4 |
| Ir1 | 500 | 10 | 2h (49) | 3h05 | 82 | 80(S) | B5 |
| Ir1 | 500 | 40 | 30'(87) | 45' | 99 | 86(S) | B6 |
| Ir2 | 500 | 40 | 15'(91) | 45' | 100 | 82(S) | B7 |
| Ir2 | 500 | 10 | 15'(51) | 30' | 93 | 82(S) | B8 |
| Ir2 | 10 000 | 40 | 2h (43) | 4h | 95 | 82(S) | B9 |
| Ir2 | 85 000 | 40 | 24h (26) | 96h | 95 | 82(S) | B10 |
| Ir3 | 500 | 40 | 15'(47) | 30' | 96 | 82(S) | B11 |
| Ir4 | 500 | 40 | 15'(68) | 25' | 98 | 83(S) | B12 |
| Ir5 | 500 | 40 | 24h (14) | 95h | 31 | 42(S) | B13 |

What is claimed is:

1. A process for the preparation of primary or secondary amines by hydrogenation of imines with hydrogen at elevated pressure and in the presence of a dinuclear Ir(III) complex having ditertiary diphosphine ligands, halide bridges, halide and hydride ligands, or an Ir(III) halide complex salt containing ditertiary diphosphine ligands, as catalyst, wherein the catalyst corresponds to formula I or Ia or to mixtures of at least two compounds of formula I, at least two compounds of formulae I and Ia, or at least two compounds of formula Ia $$[(DIP)IrX_qY_r]_2 \qquad (I),$$

$$[(DIP)X_4]^\ominus Me^\oplus \qquad (Ia),$$

wherein

DIP is the ditertiary diphosphine ligand of a ferrocenyldiphosphine the phosphine groups of which are either bonded directly or via a bridge group —CR$_v$R$_w$— in the ortho positions of a cyclopentadienyl ring or are each bonded to a cyclopentadienyl ring of a ferrocenyl, so that a 5-, 6- or 7-membered ring is formed together with the Ir atom;

R$_v$ and R$_w$ are each independently of the other hydrogen, C$_1$–C$_8$alkyl, C$_1$–C$_4$fluoroalkyl, phenyl or benzyl, or are phenyl or benzyl each having from 1 to 3 C$_1$–C$_4$alkyl or C$_1$–C$_4$-alkoxy substituents;

X is Cl, Br or I;

Y is H;

q is a number 2 or 3 and r is 0 or 1, the sum of q+r being equal to 3; and

Me$^\oplus$ is an alkali metal cation or quaternary ammonium.

2. A process according to claim 1, wherein R$_w$ is hydrogen.

3. A process according to claims 1 and 2, wherein R$_v$ is C$_1$–C$_4$alkyl.

4. A process according to claim 3, wherein R$_v$ is methyl.

5. A process according to claim 1, wherein the ditertiary diphosphine contains at least one chiral group and is a stereoisomer or a pair of diastercoisomers.

6. A process according to claim 1, wherein the phosphine groups contain two identical or different unsubstituted or substituted hydrocarbon radicals having from 1 to 20 carbon atoms.

7. A process according to claim 1, wherein the diphosphines contain two identical or different radicals from the following group: linear or branched C$_1$–C$_{12}$alkyl; unsubstituted or C$_1$–C$_6$alkyl- or C$_1$–C$_6$alkoxy-substituted $C_5$–$C_{12}$cycloalkyl, $C_5$–$C_{12}$cycloalkyl—$CH_2$—, phenyl and benzyl; and phenyl and benzyl each substituted by halogen, $C_1$–$C_6$haloalkyl, $(C_1$–$C_{12}$alkyl$)_3$Si, $(C_6H_5)_3$Si, $C_1$–$C_6$haloalkoxy, —$NH_2$, phenyl$_2$N-, benzyl$_2$N-, morpholinyl, piperidinyl, pyrrolidinyl, $(C_1$–$C_{12}$alkyl$)_2$N-, -ammonium-$X_1^\ominus$, —$SO_3M_1$, —$CO_2M_1$, —$PO_3M_1$ or by —COO—$C_1$–$C_6$alkyl; wherein $M_1$ is an alkali metal or hydrogen and $X_1^\ominus$ is the anion of a monobasic acid, and $M_1$ is preferably H, Li, Na or K.

8. A process according to claim 1, wherein
the phosphine groups are radicals of the formula

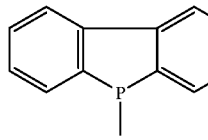 or

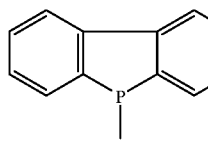 or 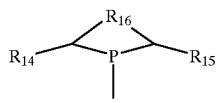

wherein m and n are each independently of the other an integer from 2 to 10 and the sum of m+n is equal to from 4 to 12.

9. A process according to claim 1, wherein the phosphine groups are radicals of the formula

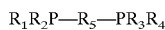

wherein $R_{16}$ is $C_1$–$C_4$alkylene, and $R_{14}$ and $R_{15}$ are each independently of the other hydrogen, $C_1$–$C_6$alkyl, $C_1$–$C_6$alkoxy, $C_1$–$C_6$haloalkyl, $C_5$- or $C_6$-cycloalkyl, or phenyl that is unsubstituted or substituted by $C_1$–$C_4$alkyl, $C_1$–$C_4$alkoxy, $C_1$–$C_4$haloalkyl or by halogen, or benzyl that is unsubstituted or substituted by $C_1$–$C_4$alkyl, $C_1$–$C_4$alkoxy, $C_1$–$C_4$haloalkyl or by halogen.

10. A process according to claim 1, wherein the ferrocenyldiphosphine corresponds to formula II $$R_1R_2P—R_5—PR_3R_4 \quad (II),$$

wherein $R_1$, $R_2$, $R_3$ and $R_4$ are each independently of the others a hydrocarbon radical having from 1 to 20 carbon atoms that is unsubstituted or substituted by $C_1$–$C_6$alkyl, $C_1$–$C_6$alkoxy, halogen, $C_1$–$C_6$haloalkyl, $(C_1$–$C_{12}$alkyl$)_3$Si, $(C_6H_5)_3$Si, $C_1$–$C_6$haloalkoxy, —$NH_2$, phenyl$_2$N-, benzyl$_2$N-, morpholinyl, piperidinyl, pyrrolidinyl, $(C_1$–$C_{12}$alkyl$)_2$N-, -ammonium-$X_{hu \ominus}$, —$SO_3M_1$, —$CO_2M_1$, —$PO_3M_1$ or by —COO—$C_1$–$C_6$alkyl, wherein $M_1$ is an alkali metal or hydrogen and $X_1^\ominus$ is the anion of a monobasic acid;

$R_1$ and $R_2$ together and $R_3$ and $R_4$ together form a $C_1$–$C_4$alkylene radical that is unsubstituted or substituted by $C_1$–$C_6$alkyl, $C_1$–$C_6$alkoxy, $C_1$–$C_6$haloalkyl, $C_5$- or $C_6$-cycloalkyl, by phenyl that is unsubstituted or substituted by $C_1$–$C_4$alkyl, $C_1$–$C_4$alkoxy, $C_1$–$C_4$haloalkyl or by halogen, or by benzyl that is unsubstituted or substituted by $C_1$–$C_4$alkyl, $C_1$–$C_4$alkoxy, $C_1$–$C_4$haloalkyl or by halogen; and $R_5$ is a radical of the formula

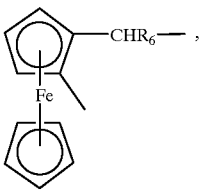 , 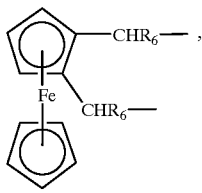 ,

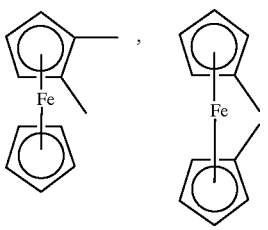

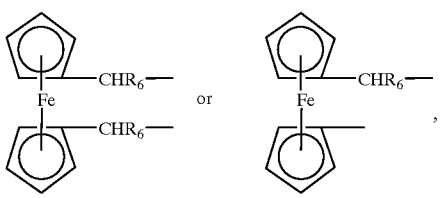

wherein $R_6$ is hydrogen, $C_1$–$C_8$alkyl, $C_1$–$C_4$fluoroalkyl, phenyl or phenyl having from 1 to 3 $C_1$–$C_4$alkyl or $C_1$–$C_4$alkoxy substituents.

11. A process according to claim 10, wherein $R_1$, $R_2$, $R_3$ and $R_4$ are identical or different radicals from the following group: $C_1$–$C_6$alkyl; cyclopentyl and cyclohexyl that are unsubstituted or have from one to three $C_1$–$C_4$alkyl or $C_1$–$C_4$alkoxy substituents; and benzyl and phenyl that are unsubstituted or have from one to three $C_1$–$C_4$alkyl, $C_1$–$C_4$alkoxy, F, Cl, $C_1$–$C_4$fluoroalkyl or $C_1$–$C_4$fluoroalkoxy substituents.

12. A process according to claim 10, wherein the disphosphine ligands DIP are those of formula III

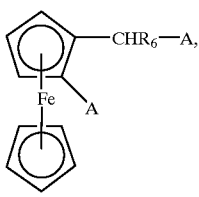    (III)

wherein $R_6$ is hydrogen or methyl; and

A represents identical or different groups —$P(R)_2$ wherein R is $C_1$–$C_6$alkyl, cyclohexyl, phenyl, benzyl, or phenyl or benzyl each having from one to three $C_1$–$C_4$alkyl, disubstituted amino, $C_1$–$C_4$alkoxy, —$CF_3$ or partially or completely fluorinated $C_1$–$C_4$alkoxy substituents.

13. A process according to claim 12, wherein the diphosphine of formula III is chiral and $R_6$ is $C_1$–$C_4$alkyl, or phenyl or benzyl each having from one to three $C_1$–$C_4$alkyl or $C_1$–$C_4$-alkoxy substituents, A represents identical or different groups —$P(R)_2$ wherein R is branched $C_3$–$C_6$alkyl, cyclohexyl, phenyl, benzyl, or phenyl or benzyl each having from one to three $C_1$–$C_4$alkyl, $C_1$–$C_4$dialkylamino, $C_1$–$C_4$alkoxy, —$CF_3$ or partially or completely fluorinated $C_1$–$C_4$alkoxy substituents.

14. A process according to claim 13, wherein R in the group $P(R)_2$ is phenyl or substituted phenyl.

15. A process according to claim 1, wherein the diphosphines are selected from the following group:

{(R)-1-[(S)-2-(diphenylphosphino)ferrocenyl]}ethyl-di (3,5-dimethyl-phenyl)phosphine {(R)-1-[(S)-2-(diphenylphosphino)ferrocenyl]}ethyl-di (3,5-dimethyl-4-N,N-dipropylaminophenyl)phosphine {(R)-1-[(S)-2-(diphenylphosphino)ferrocenyl]}ethyl-di (3,5-di-iso-propyl-4-N,N-dimethylaminophenyl) phosphine {(R)-1-[(S)-2-(diphenylphosphino)ferrocenyl]}ethyl-di (3,5-di-iso-propyl-4-N,N-dibenzylylaminophenyl) phosphine {(R)-1-[(S)-2-(diphenylphosphino)ferrocenyl]}ethyl-di (3,5-dimethyl-4-N,N-dibenzylylaminophenyl) phosphine {(R)-1-[(S)-2-(diphenylphosphino)ferrocenyl]}ethyl-di (3,5-dimethyl-4-(1'-pyrrolo)phenyl)phosphine {(R)-1-[(S)-2-(diphenylphosphino)ferrocenyl]}ethyl-di (3,5-dimethyl-4-N,N-dipentylaminophenyl)phosphine {(R)-1-[(S)-2-(diphenylphosphino)ferrocenyl]}ethyl-di (3,5-dimethyl-4-N,N-dimethylaminophenyl)phosphine {(R)-1-[(S)-2-di(4-methoxyphenyl)phosphino) ferrocenyl]}ethyl-di(3,5-dimethyl-4-N,N-dimethylaminophenyl)phosphine and especially {(R)-1-[(S)-2-(diphenylphosphino)ferrocenyl]}ethyl-di (3,5-dimethyl-phenyl)phosphine.

16. A process according to claim 1, wherein the catalysts are those of formula Ib

[(DIP)IrI$_2$H]$_2$ (Ib)

wherein DIP is as defined in claim 1.

17. A process according to claim 1, wherein the imines are imines of formula IV

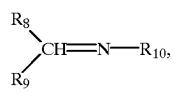

(IV)

wherein $R_{10}$ is linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and $NR_{11}$; a $C_7$–$C_{16}$aralkyl bonded via an alkyl carbon atom, or $C_1$–$C_{12}$alkyl substituted by said cycloalkyl or heterocycloalkyl or heteroaryl;

or wherein $R_{10}$ is $C_6$–$C_{12}$aryl, or $C_4$–$C_{11}$heteroaryl bonded via a ring carbon atom and having 1 or 2 hetero atoms in the ring; $R_{10}$ being unsubstituted or substituted by —CN, —$NO_2$, F, Cl, $C_1$–$C_{12}$alkyl, $C_1$–$C_{12}$alkoxy, $C_1$–$C_{12}$alkylthio, $C_1$–$C_6$haloalkyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —$CONR_{12}R_{13}$ or by —$COOR_{12}$, and the aryl radicals and the aryl groups in aralkyl, aralkoxy and aralkylthio in turn being unsubstituted or substituted by —CN, —$NO_2$, F, Cl, $C_1$–$C_4$-alkyl, -alkoxy, -alkylthio, —OH, —$CONR_{12}R_{13}$ or by —$COOR_{12}$;

$R_{12}$ and $R_{13}$ are each independently of the other hydrogen, $C_1$–$C_{12}$alkyl, phenyl or benzyl, or $R_{12}$ and $R_{13}$ together are tetra- or penta-methylene or 3-oxapentylene;

$R_{11}$ has independently the same meaning as given for $R_{12}$;

$R_8$ and $R_9$ are each independently of the other a hydrogen atom, $C_1$–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —$CONR_{12}R_{13}$ or by —$COOR_{12}$; $C_6$–$C_{12}$aryl or $C_7$–$C_{16}$aralkyl each of which is unsubstituted or substituted as $R_{10}$, or —$CONR_{12}R_{13}$ or —$COOR_{12}$ wherein $R_{12}$ and $R_{13}$ are as defined hereinbefore; or $R_{10}$ is as defined hereinbefore and $R_8$ and $R_9$ together are alkylene having from 2 to 5 carbon atoms that is optionally interrupted by 1 or 2 —O—, —S— or —$NR_6$— radicals, and/or unsubstituted or substituted by =O or as indicated above for $R_8$ and $R_9$ in the meaning of alkyl, and/or condensed with benzene, pyridine, pyrimidine, furan, thiophene or pyrrole; or $R_9$ is as defined hereinbefore and $R_9$ and $R_{10}$ together are alkylene having from 2 to 5 carbon atoms that is optionally interrupted by 1 or 2 —O—, —S— or —$NR_{11}$— radicals, and/or unsubstituted or substituted by =O or as indicated above for $R_8$ and $R_9$ in the meaning of alkyl, and/or condensed with benzene, pyridine, pyrimidine, furan, thiophene or pyrrole.

18. A process according to claim 17, wherein $R_8$ and $R_9$ are different from each other.

19. A process according to claim 17, wherein, in formula IV, $R_{10}$ is 2,6-di-$C_1$–$C_4$alkylphen-1-yl, $R_8$ is $C_1$–$C_4$alkyl, and $R_9$ is $C_1$–$C_4$alkyl, $C_1$–$C_4$alkoxymethyl or $C_1$–$C_4$alkoxyethyl.

20. A process according to claim 17, wherein the imines are imines of the formulae

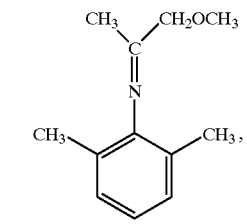

(VIa)

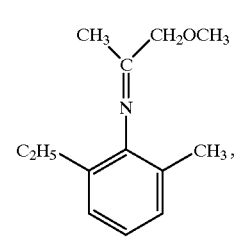

(VIb)

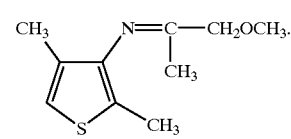

(VIc)

21. A process according to claim 1, wherein the molar ratio of imine to iridium catalyst is from 1 000 000 to 10.

22. A process according to claim 21, wherein the molar ratio of imine to iridium catalyst is from 500 000 to 20.

23. A process according to claim 21, wherein the molar ratio of imine to iridium catalyst is from 200 000 to 100.

24. A process according to claim 21, wherein the molar ratio of imine to iridium catalyst is from 100 000 to 100.

25. A process according to claim 1, wherein the reaction temperature is from −20 to 100° C.

26. A process according to claim 1, wherein the hydrogen pressure is from $2 \times 10^5$ to $1.5 \times 10^7$ Pa.

27. A process according to claim 1, wherein the reaction is carried out in the presence of a solvent.

* * * * *